United States Patent [19]

McCoy

[11] Patent Number: 5,283,767

[45] Date of Patent: Feb. 1, 1994

[54] AUTONOMOUS OCEANOGRAPHIC PROFILER

[76] Inventor: Kim McCoy, P.O. Box 191,, Carmel, Calif. 93921

[21] Appl. No.: 843,852

[22] Filed: Feb. 27, 1992

[51] Int. Cl.$^5$ .......................... H04B 1/59; G01S 5/00
[52] U.S. Cl. .................................. 367/004; 73/170.34; 114/331; 441/29
[58] Field of Search ..................... 367/3, 4; 73/170.34; 441/1, 21, 28, 29; 114/328, 331

[56] References Cited

U.S. PATENT DOCUMENTS

| | | | |
|---|---|---|---|
| 3,731,262 | 5/1973 | Blake, Jr. ................................ | 367/3 |
| 4,191,049 | 3/1980 | Bowditch et al. ............... | 73/170.34 |
| 4,691,305 | 9/1987 | Kuck ....................................... | 367/3 |

OTHER PUBLICATIONS

T. Duda et al., "The Cartesian Diver: A Self-Profiling Langrangian Velocity Recorder", Journal of Atmospheric and Oceanic Technology, vol. 5, No. 1, pp. 16–33, Feb. 1988.

T. Rossby et al., "The RAFOS System", Journal of Atmospheric and Oceanic Technology, vol. 3, No. 4, pp. 672–679, Dec. 1986.

D. Echert et al., "The Autonomous Ocean Profiler: A Current-Driven Oceanographic Sensor Platform", IEEE Journal of Oceanic Engineering, vol. 14, No. 2, pp. 195–202, Apr. 1989.

Battelle & Ocean Sensor, Inc., "An Expendable CTD Profiler with ARGOS Data Link and GPS Capability".

*Primary Examiner*—Daniel T. Pihulic
*Attorney, Agent, or Firm*—Baker, Maxham, Jester & Meador

[57] ABSTRACT

There is disclosed a portable free drifting oceanographic instrument package for cyclically collecting oceanic and/or fresh water environmental data over a range of depths. The instrument includes, in combination, a submersible housing having mounted thereto (1) a sensor suite for collecting selected environmental data relating to a surrounding medium, (2) a data storage resource for storing environmental data sensed by the sensor suite, (3) a dive control system for controllable positioning the apparatus to a selected depth, (4) a data communications system for facilitating full duplex communication between the apparatus and a remote communications site, (5) a locating system for determining the position of the apparatus, (6) a rechargeable power system for providing operational power to the instrument package, (7) an energy collection system with no moving parts for collecting energy from the environment to recharge the power system, and (8) a system controller for controlling operations of the sensor suite, the data storage resource, the dive control system, the data communications system, the locating system, the rechargeable power system and said energy collection system.

26 Claims, 2 Drawing Sheets

AUTONOMOUS OCEANOGRAPHIC PROFILER

BACKGROUND OF THE INVENTION

The present invention relates to the remote measuring of oceanic (and near surface atmospheric) data under the control of a teleoperator or data acquisition center. More particularly, the invention concerns an autonomous, generally free drifting, data acquisition instrument for extended collection of environmental data from an ocean or fresh water body.

The physical, biological and geological properties of the world's oceans and large fresh water bodies are severely undersampled in time and space. At present, only limited short-term data sets of small portions of such bodies are available. This lack of comprehensive oceanographic information is directly attributable to the high cost of data acquisition. Historically, data collection has been completed using instruments lowered from ships, or moored instrument arrays which must be recovered. The cost of operating a manned vessel on the high seas is prohibitive. Moreover, vessel availability cannot always be assured. Oceanographic experiments are thus constrained in many cases by factors other than the phenomenon which is intended for study.

In light of the foregoing, it is apparent that a lower cost per data point could be attained if the data acquisition process relied less on traditional ship based measurement techniques. To date, there have been various proposals of data acquisition devices which obtain environmental data without the need for a manned vessel to place the device or acquire data therefrom. However, there have been no proposals for a completely autonomous data acquisition instrument capable of: (1) cyclically profiling environmental data over a range of depths, (2) acquiring geographic positions, (3) conducting two way communications, and (4) collecting additional energy over extended periods of time.

With current systems, data collection and distribution is limited by telemetry and power systems, which reduce the amount of data collected and the life of the instrument. There is no provision for bi-directional communications and locating capability, and these instruments must therefore be preprogrammed or moored at fixed locations for later retrieval, all at increased expense. Duda, et al., "The Cartesian Diver: A Self-Profiling Lagrangian Velocity Recorder", Jour. of Atmos. and Ocean. Tech., Vol. 5, No. 1 (Feb 1988), describes a device to vertically profile several parameters. The data are stored in the device for later retrieval. There is no provision for determining location.

Rossby, et al., "The RAFOS System", Jour. of Atmos. and Ocean. Tech., Vol. 3, No. 4 (Dec 1986), describes a subsurface free drifting device (RAFOS) which uses acoustic (experiment specific) tracking methods for determining location of the unit from a remote site (the device has no self-locating capability). Data is communicated using the ARGOS satellite system. Only a small amount of data is stored in RAFOS and the ARGOS satellite data transmission occurs only at the end of a drifting period. The ARGOS system is transmit only, and limited to approximately 256 bits/10 minute satellite pass with a maximum of thirty passes per day at the earth's poles and as low as six passes at the equator. It is significant that an ARGOS based instrument such as RAFOS does not know where it is and hence cannot make a decision based on position. The lack of instrument knowledge of position adds to the uncertainty of when a polar orbiting satellite will be available for data transmission. This uncertainty requires a high level of redundant data transmission and thus increases the amount of energy needed per bit of useful data.

Davis et al (Scripps Institute of Oceanography) have constructed a Lagrangian drifter (ALACE) similar to RAFOS also using ARGOS for data telemetry as well as location determination (from a remote site).

None of the foregoing systems include energy collection, global positioning capability (GPS) or global bi-directional telecommunications. Accordingly, persons skilled the art will recognize that there remains a compelling need for an autonomous controllable, oceanographic data sampling system capable of long term, free ranging movement through oceans and large fresh water bodies.

SUMMARY OF THE INVENTION

The present invention is directed to and advantageously provides a portable free drifting instrument package for cyclically collecting oceanic and/or fresh water environmental data over a range of depths. In preferred embodiments thereof, the instrument package includes, in combination, a frame or housing having mounted thereto (1) a sensor suite for collecting selected environmental data relating to a surrounding medium, (2) a data storage resource (i.e. memory) for storing environmental data sensed by the sensor suite, (3) a dive control system for vertically positioning the apparatus, (4) a data communications system for facilitating bi-directional (full duplex) communications between the apparatus and a remote communications site, (5) a location control system for determining the navigational position of the apparatus, (6) a rechargeable power system for providing operational power to the instrument package, (7) an energy collection system for collecting energy from the environment to recharge the power system, and (8) a system controller for controlling operations of the sensor suite, the data storage resource, the dive control system, the communications system, the location system, the rechargeable power system and the energy collection system.

The instrument package makes it possible to reduce the cost of acquiring oceanographic data. This device, much like an earth satellite in space, is not intended to be retrieved, and need not be retrieved, because all data acquisition and control functions are available to the remote operator. The useful life of the instrument and length of deployment are greatly extended to multiple years by using an energy storage and collection system. The amount of stored energy required and hence, the instrument volume and associated cost of the instrument, are greatly reduced.

The use of Lagrangian transport (drifting) and vertical (depth) control facilitates collection of data over long periods and large areas without an onboard horizontal propulsion system being necessary. Dive control (ballasting for vertical movement) allows the operator or operating system to complete longterm data collection at the surface, on the bottom, midwater or any combination thereof. The control system buffers the collected data and transmits the data, based on user request, preprogrammed time, environmental conditions or geographical location. Bi-directional communications facilitate remote reprogramming (e.g., mission changes) based upon newly acquired data or geographical location.

DETAILED DESCRIPTION OF THE PREFERRED EMBODIMENTS

Figure 1:
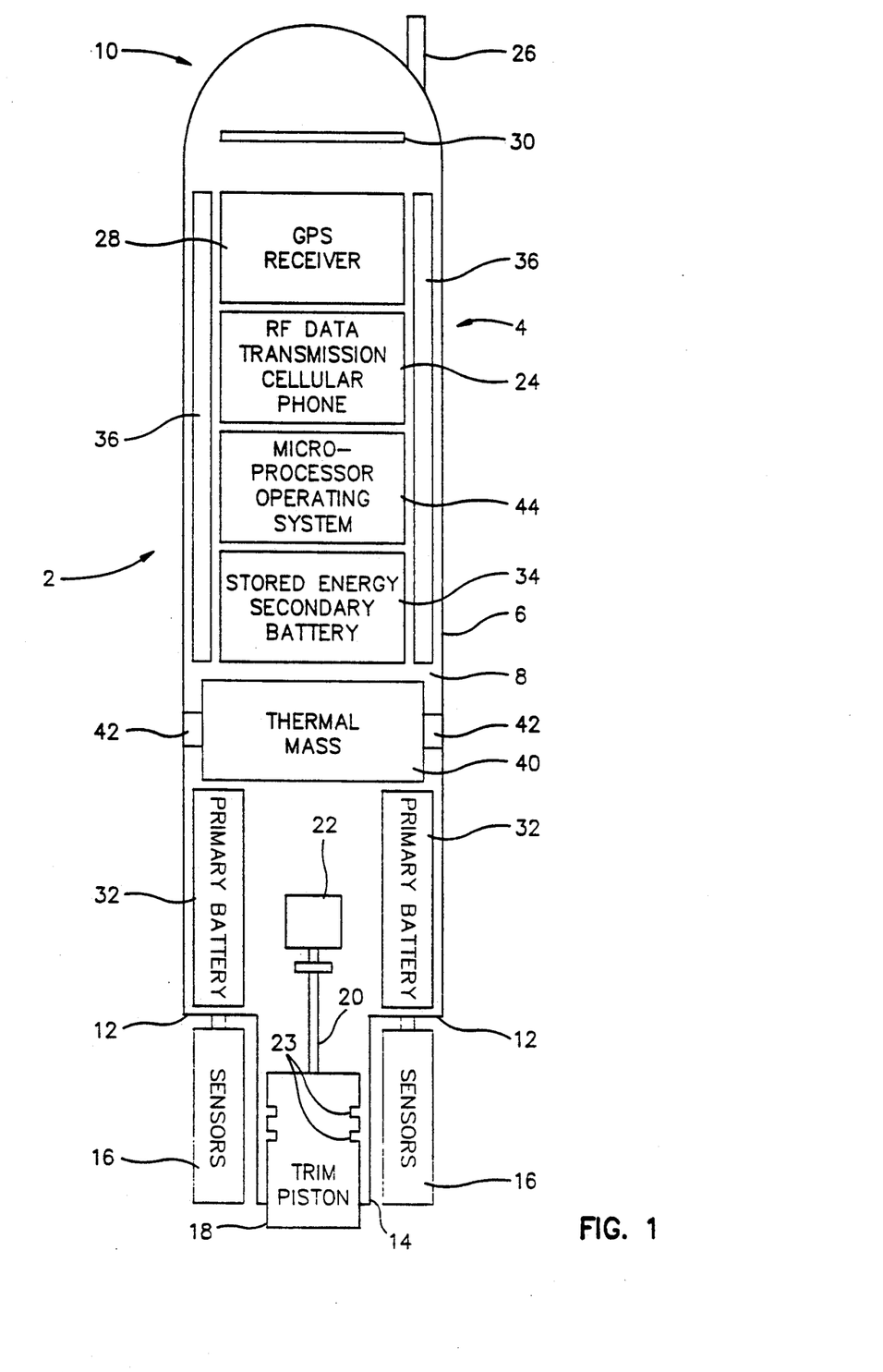
FIG. 1 is an elevated side view schematically illustrating an autonomous data acquisition instrument constructed in accordance with the present invention.

Referring now to FIG. 1, an autonomous teleoperated data acquisition system includes a portable free drifting instrument package 2 for cyclically collecting oceanic and/or fresh water environmental data over a range of depths. The instrument package 2 is conveniently formed as an arrangement of components mounted on or in a submersible frame or housing 4. The submersible frame 4 may take a number of shapes and configurations. For example, the frame may be formed as an open structure having plural frame members for mounting instrument components in a convenient portable package. In that configuration, the individual components would themselves be water-tight and pressure-resistant while the submersible frame itself would not. Alternatively, the submersible frame 4 could be formed as a sealed structure or pressure housing 6 providing a water tight cavity within which the instrument components would be protected from the surrounding environment. The housing 6 could be formed in a variety of shapes, but is illustrated in FIG. 1 as being generally cylindrical so as to define a cylindrical cavity 8 within which system components are placed. The housing 6 may be advantageously formed and composed of optionally transparent material, such as glass, ceramic or acrylic plastic. Positioned at the upper end of the housing 6 is an antennae module 10 which may be integrally formed with or separately mounted and sealed to the housing 6. There is formed at the lower end of the housing section 6 a sensor mounting platform 12 and a hollow dive control cylinder 14. These components are mounted and sealed to the housing to provide a water tight configuration.

A sensor suite including plural data sensors 16 is mounted to the sensor mounting platform 12. The sensors 16 are conventional in nature and may be adapted to sense a variety of environmental data, including temperature, pressure, salinity, conductivity and density, as well as optical, chemical, geological, surface meteorological and acoustic data. The sensors 16 produce electrical analog or digital signals providing a quantitative representation of conditions to be sensed. Whether the output signal is digital or analog depends on the design specifications of the sensors themselves, which may all be off-the-shelf products available to persons skilled in the art.

The dive control cylinder 14 located at the bottom of the housing 6 supports a trim control piston 18 for slidable movement therein. The trim control piston 18 is reciprocally driven by a threaded member 20 which is rotatable and connected to a reversible DC drive motor 22. For sealing purposes, the piston 18 includes one or more "O"-rings 23 to prevent water ingress into the cylindrical housing cavity 8. The motor 22 may be selectively operated to rotate the threaded member 20, which in turn causes the dive control piston 18 to translate through the dive control cylinder 14. This has the effect of altering the volume, and thus the ballasting of the instrument package 2 so that the instrument ascends or descends in its water environment in accordance with the change in ballast. Thus, a dive control system is advantageously provided.

The instrument package 2 further includes a data communications module 24 mounted within the cavity 8 to the housing 6. The data communications module 24 preferably includes a cellular telephone communications device for facilitating bi-directional (full duplex 1200 baud and greater) communication between the instrument package 2 and a remote communications site. Telephony, in comparison to ARGOS and other existing transmit-only satellite data networks, has the advantage of substantially reducing telemetry energy costs and dramatically increasing the amount of data that can be transmitted.

The present invention takes advantage of current efforts to extend the cellular telephone network to global coverage. Low Earth Orbit (LEO) satellites and higher data rates will reduce the amount of energy per bit required for transmission. Companies such as Motorolla, TRW, Orbcomm and Leosat are presently undertaking such projects. With the systems that are currently in place, is possible to use cellular telecommunications within the near coastal areas. With the global coverage provided, it will be possible to transmit global oceanographic data via a modem (modulator/demodulator) and a cellular telephone, which also eliminates the additional cost of a dedicated ground receiver required in existing VHF and other systems. This advance will greatly increase the bit transmission rate and lower the amount of energy required per bit of information transmitted.

The data communications module 24 is operatively connected to a transmit/receive antenna 26 extending from the antenna module 10. Both the cellular data transmission module 24 and transmit/receive antenna 26 are conventional in design. An effective data communications system is thus provided.

To facilitate the accurate correlation of environmental data with geographic position, the instrument package 2 is provided with a locating system which includes a global positioning system (GPS) receiving device 28. The GPS receiver is mounted within the cavity 8 to the housing 6. Several companies (Magnavox, Rockwell, Magellan, Trimble) are marketing receiving devices for a Global Positioning System. These devices are typically small (2.5"×4") and low power (5 volts, 0.25 amps). They are capable of being interrogated over a serial I/O port. Both position (latitude and longitude) and precise time are available. In operation, the GPS receiving device obtains a pseudo random code signal from plural satellites in orbit around the earth. The satellites further provide a signal representing the precise time (GMT). The satellites are positioned in different orbits. The GPS receiver-calculated position error is accurate to within typically 100 meters or less. The GPS device determines its position as opposed to the less accurate ARGOS system which facilitates the external calculation of position. It is significant that an ARGOS based location device does not know where it is.

The locating system further includes a GPS antenna device 30 mounted in the antenna module 10. The antenna 30 is formed by depositing a thick film conductor on a ceramic substrate. The substrate is thereafter covered by a layer of non-conductive glass over the conductive antenna pattern. Glass is virtually impervious to water and is orders of magnitude more stable than epoxies or other encapsulating compounds. This configuration allows the GPS antenna to be constructed and deployed to full ocean depths without a pressure housing, thus greatly reducing the volume of the antenna assembly.

The data acquisition instrument 2 is powered by a rechargeable power system. The power system may include a primary battery 32 and a secondary rechargeable battery 34. The primary battery 32, preferably conventional in nature, is used to support metabolic operations such as system control and sensor operations, wherein power (energy per unit time) demand is low. The secondary battery 34, also conventional in nature, is a rechargeable battery used to perform high power operations such as trim control and data communications. Both batteries are mounted within the cavity 8 to the housing 6.

The total volume of the instrument package 2 determines the amount of energy required to make a dive to a given depth. The amount of buoyancy created (proportional to energy expended) establishes the time required to complete a dive cycle. The energy density of the device determines the number of cycles to a given depth. Hence, it is important to keep the volume as small as possible and the energy density near constant as a function of time. If the instrument utilizes only stored primary energy, the energy density decreases with time as the number of cycles through an oceanic density gradient increases (i.e., the battery capacity decreases but the volume remains constant).

Accordingly, an energy collection system is implemented so that the energy expended during a dive or surface data transmission period may be regained via collection systems. The instrument package 2 utilizes both solar (photovoltaic) and electro-thermal (Peltier Effect) devices with no moving parts. Although such schemes are inefficient by most standards, total efficiency of only a few percent is adequate for the energy budget for a cycling device with a cycling frequency of less than once per day to 1000 meter depths.

A typical data acquisition cycle to 1000 meters would expend approximately 1300 Joules of energy. The density in the most of the world's ocean varies approximately 5 Sigma-T units. This correlates to approximately 0.5% density difference between the surface and 1000 meter waters. Correspondingly, the volume variation provided by the dive piston need only be about 50 cubic centimeters for a 10 liter instrument volume. The 1300 Joules of energy should thus be sufficient to dive (100 J), acquire data during decent and ascent (700 J), return to the surface (240 J), acquire a position from GPS (200 J), and transmit the data (60 J).

The solar energy component of the energy collection system may be configured to include plural arrays of low light sensitive or conventional solar cells 36. These arrays are preferably mounted at the upper end of the cavity 8 to the housing 6, so as to be exposed to maximum solar energy upon surfacing. The arrays 36 may also be used as an available light sensor by monitoring the voltage. There are many manufacturers of solar cell products suitable for use in the instrument package 2. Because light is rapidly diffused in the ocean. The solar cells need not be facing directly toward the sun. As long as the critical angle of the transparent housing (e.g. glass, ceramic, or acrylic plastic) is not exceeded, energy is available for collection radially in the horizontal plane. To facilitate solar energy collection, the instrument package 2 may remain at the surface for extended periods of time (e.g., multiple hours to days).

The instrument package 2 may also be positioned slightly below the water surface during solar recharging. Most of the infrared energy of the sun is absorbed within the first few millimeters of the ocean surface. Photovoltaic cells have a maximum absorption outside these wavelengths. Glass, transparent plastics and some ceramics, which have excellent mechanical properties, may be used to form a water-tight seal over the solar cells, and do not exhibit excessive absorption at photovoltaic significant wavelengths. Thus, the instrument package 2 can collect solar energy in a similar manner as a space satellite exploits solar energy.

The extraction of a few hundred milliwatts of power for several hours per days should be possible because solar radiation is approximately 1,000 watts per square meter at the surface of the ocean. It has been determined that the instrument package 2 can be operated on 0.035 square meters (350 square centimeters) of exposed commercially available solar cells. At 10 percent solar cell efficiency, the available power is 3.5 watts continuous. With a 70 percent charging efficiency, 2.5 watt hours of energy would be collected per hour of solar exposure. It should further be noted that these numbers (350 square centimeters and 1 hour per day) are very conservative, and actually underestimate the instrument surface available for solar cells and time of exposure.

The second method of energy collection utilized by the instrument package 2 is based on thermal gradient. In most of the world's oceans, the temperature decreases with depth. In Polar regions this relationship is reversed. The oceans's thermal gradient may be exploited. The instrument package 2 takes advantage of this temperature gradient using a thermoelectric "Peltier Effect" thermal gradient device 38 mounted in the cavity 8 to the housing 6. The Peltier device 38 has no moving parts and takes advantage of a temperature difference to produce an electrical output, in accordance with the "Peltier Effect". The Peltier Effect is a phenomenon whereby a temperature gradient across the Peltier device results in the development of an electrical potential proportional to the temperature difference. One side the Peltier device 38 is in thermal contact with a thermal mass 40 and the other side is in thermal contact with the surrounding water medium. The rechargeable battery 34 is connected in series with the Peltier device 38 so as to be recharged when an electrical current flows in this circuit. The thermal mass can be advantageously made with water, ethylene glycol or the like as a heat storage medium to provide a maximum thermal differential relative to the surrounding medium, and thus a maximum voltage differential across the Peltier device.

In the instrument package 2, a thermal gradient can be provided from the thermal mass 40 through the Peltier device to the surrounding environment. The instrument package 2, over a period of hours, will reach thermal equilibrium with the water around it (i.e., the thermal mass 40 will be at the same temperature as the surrounding water medium). As the instrument package ascends or descends, there will be a temperature difference which can be exploited, and energy extracted by use of the Peltier device 38. On each cycle, energy can be extracted provided there is a vertical thermal gradient. Typically, ocean water temperature is 4° C. at 1000 meters depth and 20° C. at the surface. The heat flux is reversed in direction during ascent. This should not be confused with adiabatic thermal differences that arise when transmitting through a pressure gradient. Peltier devices are conventional in nature and are available from various manufacturing sources.

The operation of the instrument package 2 is controlled by a system controller which is preferably a programmable microprocessor 44. The processor 44 is mounted within the cavity 8 to the housing 6. It is electrically connected to and controls the operation of the sensor suite, the dive control system, the data communications system, the locating system, the rechargeable power system and the energy collection system. The processor 44 is conventional in nature and may be constructed from commercially available micro-processor devices having a central processing unit (CPU) and appropriate input/output (I/O) capability. Such devices have low power requirements (e.g., 350 milliwatts full power, 1 milliwatt quiescent power).

The processor 44 communicates with a data storage resource 46. The data storage resource stores an operational control program and provides operational memory including buffers, stack memory and the like. It also serves as a buffer for environmental data collected by the system. The data storage resource may include random access memory (RAM), read only memory (ROM), static random access memory (SRAM) and/or electrically erasable programmable read only memory (EEPROM). The control program includes control logic for directing the operations of the sensor suite, the dive control system, the data communications system, the location system, the rechargeable power system and the energy collection system. Persons skilled in the art will appreciate that appropriate control programming code can be written in routine fashion.

Figure 2:
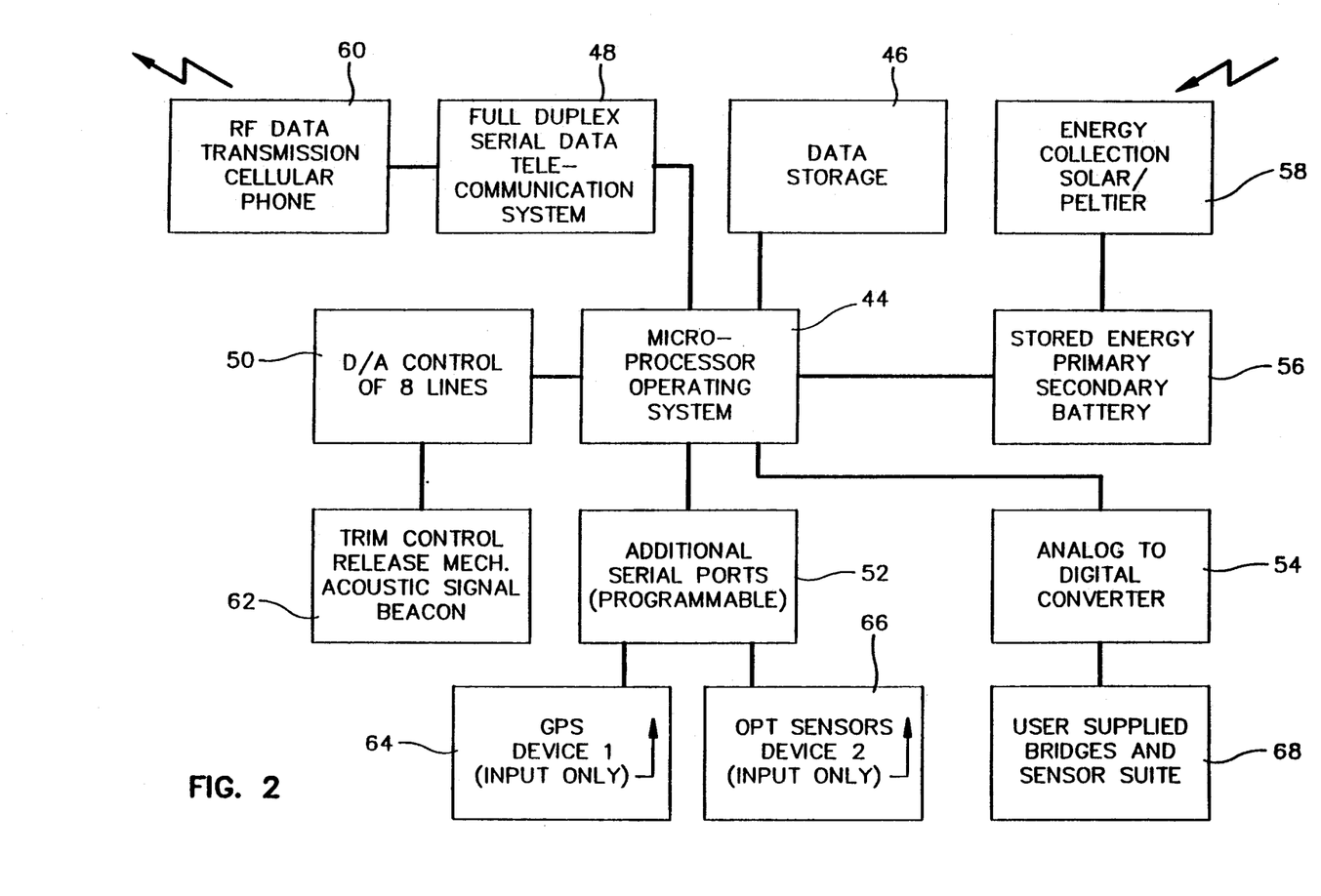
FIG. 2 is a block diagram showing functional components of the data acquisition instrument of FIG. 1.

Referring now to FIG. 2, the microprocessor system 44 is shown to be electrically connected with the data storage resource 46, a telecommunication system 48, a digital/analog control interface 50, a serial port interface 52, an analog to digital convertor 54, a rechargeable energy storage system 56 and an energy collection system 58. The functions of the data storage resource 46 have been described. The telecommunication system 48 includes an RF data transmission cellular telephone system 60 including the data transmission module 24 and the transmit/receive antenna 26 previously discussed. The telecommunication system 48 further includes a modem (modulator/demodulator) (not shown) that may be integrated with the data transmission module 24. The digital/analog controller interface 50 provides interface control over a plurality of data lines (e.g., 8) between the processor 44 and selected devices operating under processor control. These devices are shown in the functional block 62 of FIG. 2. They include the trim control system previously described. Other devices could be provided to facilitate recovery of the instrument package upon completion of a mission or in the event of a malfunction or emergency. Examples include a ballast release surfacing mechanism or an acoustic or visual signal (e.g. strobe) beacon, as illustrated in FIG. 2.

The serial interface 52 is programmable and is used to provide serial I/O between the processor 44 and selected peripheral devices. These devices would include the GPS previously described locating system, which is illustrated as function block 64 in FIG. 2. Other devices might include sensors whose output is digital in nature. These optional sensors are illustrated by function block 66 in FIG. 2.

The analog to digital converter 54 provides I/O communications between the processor 44 and the sensor suite previously discussed. The sensor suite includes the sensors 16, which provide an analog output signal that must be converted to digital form by the analog to digital converter 54. The sensor suite further includes user supplied bridges (e.g., Wheatstone bridges) for indicating sensor readings. The rechargeable power system and energy collection have been described. They are illustrated as function blocks 56 and 58 in FIG. 2, respectively.

The processor control system 44 is programmed to control the instrument package 2 for free drifting, autonomous teleoperated data acquisition in an ocean or fresh water body. It is anticipated that the instrument package 2 will be launched from a ship or low flying aircraft at a desired geographic location, following which the device will drift by Lagrangian transport for an extended period, i.e., several years. The control system processor 44 controls the instrument package 2 to cyclically descend and ascend over a range of depths. For example, the processor system 44 may control the device to cycle to a depth of 1000 meters over a period of days. The processor system 44 determines the depth of the instrument package 2 by sampling the sensor suite 62 which preferably includes a pressure sensor. The analog output of the sensor is converted to a digital signal which the processor 44 utilizes for depth readings. As the instrument package 2 descends to the predetermined depth and thereafter rises to the surface, the processor system 44 continuously or periodically samples the pressure sensor and/or selected other sensors of the suite 68 to obtain environmental readings. These inputs are buffered into the data storage resource 46. The descent and ascent velocities are governed primarily by the amount of buoyancy (positive or negative), the projected frontal area, water viscosity, and the drag coefficient in the major axis of translation of the body. Thus, for a given fluid density, a known piston displacement would correlate to a vertical profile velocity. Forming the housing 6 as a long cylindrical pressure housing with a length to diameter ratio of 10 or more would provide a low drag body during profiling. As an added feature the housing 6 would provide a stable platform for data transmission purposes.

Following one or more dive cycles, the processor system 44 controls the instrument package 2 to float on or near the surface, and to commence data communications with a remote receiving station. This communication may be commenced at a pre-arranged time or geographic location (not possible with ARGOS). It may also be commenced in conjunction with a data transmission request signal from the instrument package 2. At the surface and prior to data transmission, the processor system 44 operates the GPC receiver to determine the position of the instrument. That position is transmitted in conjunction with the environmental data from the memory 46. In order to facilitate time-designated transfer of data, the processor system 44 includes an instrument clock and a time based program. However, the instrument clock is relatively inexpensive, and it will drift significantly during the course of its operations. The GPS receiver has access to very accurate time and may be utilized to reset the instrument clock in accordance with a satellite provided signal representing exact universal time. The clock reset will synchronize the time based instrument functions and make data transmission more energy efficient.

If desired, the processor system 44 may be remotely reprogrammed via the data communication system. In this manner, the instrument package 2 could be programmed to perform site specific opportunistic data gathering missions and to communicate that data at a selectable time. At other times, it may be desireable to request an extended instrument residence time below the photic zone (typically 200 meters) to reduce biofouling. At these depths the biofouling rate is essentially zero. It is thus possible to eliminate heavy upper ocean related biofouling by periodically remaining below the level at which photo-synthesis is active (generally, at a much lower temperature). A two week residence time at depth should be sufficient to eliminate biofouling. This is very important for longterm instrument ballasting and sensor survival.

While at the surface, the processor 44 controls the solar energy collection system to recharge the secondary battery. In similar fashion, the processor 44 controls the Peltier device 38 to recharge the secondary battery when an acceptable thermal radiant condition exists between a thermal mass 40 and the surrounding medium. In this manner, the instrument package battery may be periodically recharged and its mission life extended for many months and even years over conventional systems.

Thus, an autonomous, teleoperated data acquisition system has been described. The system utilizes a combination of instrument geographic location, communication, dive control, energy collection and a programmable control system. Communications can be completed through the use of any radio device, but are preferably effected using a cellular telephone network. Geographic position is provided by a global positioning system which provides absolute latitude or relative coordinates to ground stations. The variable ballast dive control system allows the data acquisition device to achieve any position in the vertical axis (designed for but not limited to 1000 meters). This vertical control also allows repositioning in latitude and longitude using the horizontal advection in the oceans (or atmosphere). Energy collection (solar or temperature gradient) greatly extends the operational life time of the system. The microprocessor based controller allows command, control, interrogation and reprogramming of the subsystems to acquire data when and where desired.

While various preferred embodiments of the present invention have been described, it will understood that modifications and adaption thereof may occur to persons skilled in the art. Therefore, the protection afforded the invention should not be limited except in accordance with the spirit of the following claims and their equivalents.

I claim:

1. A portable free drifting instrument package for cyclically collecting oceanic and/or fresh water environmental data over a range of depths, comprising:
    a submersible housing;
    a sensor suite mounted to said housing for collecting selected environmental data relating to a surrounding medium;
    a data storage resource mounted to said housing for storing environmental data sensed by said sensor suite;
    a dive control system mounted to said housing for controllably positioning the instrument package at a selected depth;
    a data communications system mounted to said housing for facilitating bi-directional (full duplex) communication between the instrument package and a remote communications site;
    a locating system mounted to said housing for self determination of navigational position of the instrument package;
    a clock system mounted to said housing for synchronizing one or more time-based instrument functions of said instrument package;
    a clock reset system mounted to said housing for receiving a time signal from a remote source and resetting said clock system and time-based instrument functions for increased energy efficiency;
    a rechargeable power system mounted to said housing for providing operational power to the instrument package;
    an energy collection system mounted to said housing for collecting energy from the environment to recharge said power system; and
    a system controller mounted to said housing for controlling operations of said sensor suite, said data storage resource, said dive control system, said data communications system, said locating system, said rechargeable power system and said energy collection system.

2. The instrument package of claim 1 wherein said data communications system includes a cellular telephone communication device.

3. The instrument package of claim 2 wherein said controller is a digital processor and said data communications system further includes a modem (modulator/demodulator) device.

4. The instrument package of claim 1 wherein said locating system and clock reset system include a global positioning system receiver module for receiving plural time and position satellite data transmissions, said receiver module including means to determine its own position and facilitate autonomous decisions based on position.

5. The instrument package of claim 4 wherein said locating system further includes an antenna formed from a ceramic substrate, a thick film conductor pattern deposited on said substrate and a relatively thin glass covering formed over said substrate and said conductor pattern.

6. The instrument package of claim 1 wherein said energy collection system includes a horizontal and/or vertical solar collector and thermo-electric device.

7. The instrument package of claim 6 wherein said solar collector includes a plurality of photo voltaic cells.

8. The instrument package of claim 6 wherein said thermoelectric device includes a Peltier device with no moving parts.

9. The instrument package of claim 8 wherein said Peltier device includes a thermal mass in thermal communication with a surrounding medium, said thermal mass being selected to provide a voltage differential across said Peltier device proportional to a thermal differential across said thermal mass and the surrounding medium.

10. The instrument package of claim 1 wherein said rechargeable power system include as a primary power source and/or a secondary rechargeable power source, and wherein said energy collection system includes no moving parts.

11. The instrument package of claim 1 wherein said system controller includes means for controlling the instrument package to cyclically descend and ascend over a range of depths in a watery medium in which the instrument package is placed, to gather and store environmental data over said range of depths, to return to a surface location, to determine a position of the instrument package from said locating system, to make decisions based thereon, to calculate mean horizontal velocity, and to transmit said environmental data and position over said communications system when the instrument package is at a surface location.

12. A portable free drifting instrument package for cyclically collecting oceanic and/or fresh water environmental data over a range of depths, comprising:
   a submersible housing;
   a sensor suite mounted to said housing for collecting selected environmental data relating to a surrounding medium;
   a data storage resource mounted to said housing for storing environmental data sensed by said sensor suite;
   a dive control system mounted to said housing for controllably positioning the instrument package at a selected depth;
   a data communications system mounted to said housing for facilitating bi-directional (full duplex) communication between the instrument package and a remote communications site, said data communications system including a cellular telephone communication device;
   a locating system mounted to said housing for self determination of navigational position of the instrument package;
   a rechargeable power system mounted to said housing for providing operational power to the instrument package;
   an energy collection system mounted to said housing for collecting energy from the environment to recharge said power system; and
   a system controller mounted to said housing for controlling operations of said sensor suite, said data storage resource, said dive control system, said data communications system, said locating system, said rechargeable power system and said energy collection system.

13. The instrument package of claim 12 wherein said controller is a digital processor and said data communications system further includes a modem (modulator/demodulator) device.

14. A portable free drifting instrument package for cyclically collecting oceanic and/or fresh water environmental data over a range of depths, comprising:
   a submersible housing;
   a sensor suite mounted to said housing for collecting selected environmental data relating to a surrounding medium;
   a data storage resource mounted to said housing for storing environmental data sensed by said sensor suite;
   a dive control system mounted to said housing for controllably positioning the instrument package at a selected depth;
   a data communications system mounted to said housing for facilitating bi-directional (full duplex) communication between the instrument package and a remote communications site;
   a locating system mounted to said housing for self determination of navigational position of the instrument package, said locating system including a global positioning system receiver module for receiving plural satellite data transmissions, said receiver module including means to determine its own position and facilitate autonomous decisions based on position, and said locating system further including an antenna formed from a ceramic substrate, a thick film conductor pattern deposited on said substrate and a relatively thin glass covering formed over said substrate and said conductor pattern;
   a rechargeable power system mounted to said housing for providing operational power to the instrument package;
   an energy collection system mounted to said housing for collecting energy from the environment to recharge said power system; and
   a system controller mounted to said housing for controlling operations of said sensor suite, said data storage resource, said dive control system, said data communications system, said locating system, said rechargeable power system and said energy collection system.

15. An automated method for obtaining environmental data in an ocean or fresh water body comprising the steps of:
   deploying into an ocean or fresh water body a portable free drifting instrument package including sensor means for collecting environmental data samples, storage means for storing environmental data samples, dive control means for positioning the instrument package over a range of depths, data communication means for providing data communications with one or more remote receiving stations, location means for determining a position of the instrument package, rechargeable power means for providing operational power to the instrument package, energy collection means for recharging said power source, said system control means for controlling operation of said sensor means, said storage means, said dive control means, said data communications means, said locating means, said rechargeable power means, and said energy collection means;
   controlling said instrument package to obtain and store environmental data samples over a selected range of depths while freely drifting in the ocean or fresh water body;
   controlling said instrument package to periodically surface;
   controlling said instrument package, upon surfacing, to obtain a position;
   controlling said instrument package to transmit said position and said stored environmental data samples to a remote receiving station in response to said instrument package drifting to a predetermined geographical position; and
   controlling said energy collection system to periodically recharge said rechargeable power supply, as necessary.

16. An automated method for obtaining environmental data in an ocean or fresh water body comprising the steps of:

deploying into an ocean or fresh water body a portable free drifting instrument package including sensor means for collecting environmental data samples, storage means for storing environmental data samples, dive control means for positioning the instrument package over a range of depths, data communication means for providing data communications with one or more remote receiving stations, location means for determining a position of the instrument package, system clock means for synchronizing one or more time-based instrument functions of the instrument package, system clock reset means for receiving a time signal from a remote source and resetting said system clock means and time-based instrument functions, rechargeable power means for providing operational power to the instrument package, energy collection means for recharging said power source, said system control means for controlling operation of said sensor means, said storage means, said dive control means, said data communications means, said locating means, said rechargeable power means, and said energy collection means;

controlling said instrument package to obtain and store environmental data samples over a selected range of depths while freely drifting in the ocean or fresh water body;

controlling said instrument package to periodically surface;

controlling said instrument package, upon surfacing, to obtain a position and reset said system clock means for energy efficiency;

controlling said instrument package to transmit said position and said stored environmental data samples to a remote receiving station; and controlling said energy collection system to periodically recharge said rechargeable power supply, as necessary.

17. The method of claim 16 wherein the step of transmitting a location and said stored environmetnal data samples is performed in response to a user request transmitted from a remote receiving station.

18. The method of claim 16 wherien the step of transmitting a location and said stored environmental data is performed in response to the occurrence of a predetermined time.

19. The method of claim 16 wherien the step of transmitting the location and said stored environmental data is performed in response to said instrument package drifting to a predetermined geographical location.

20. The method of claim 16 further including the step of controlling the instrument package to reside below the photic zone for a period of time sufficient to substantially eliminate biofouling.

21. A portable free drifting instrument package for cyclically gathering environmental information over a selected range of depths in an ocean or fresh water body, comprising:

a submersible housing having mounted thereto an upper antenna module and a sensor mounting platform;

a sensor suite mounted to said sensor mounting platform for collecting selected environmental data relating to a surrounding medium;

a data storage resource including a digital memory mounted in said housing for storing environmental data sensed by said sensor suite;

a dive control system for controllably positioning the instrument package over a range of depths, said dive control system including a ballasting control cylinder extending through said sensor mounting platform, a trimming piston slideably arranged in said ballast control cylinder and a drive motor mounted in said housing and operatively connected to said trimming piston;

a data communications system including a cellular telephone communications device mounted in said housing for facilitating bi-directional (full duplex) communication between the instrument package and a remote communications site, said data communications system further including an antenna mounted to said antenna module;

a locating system including a global positioning system receiving device mounted in said housing for determining a navigational position of the instrument package, said navigational control system including antennae mounted to said antenna module, an antenna being formed from a thick film conductor pattern mounted on a ceramic substrate with a thin glass covering mounted over said conductor pattern and substrate;

a rechargeable power system including a primary battery and a secondary rechargeable battery mounted in said housing for providing operational power to the instrument package;

an energy collection system mounted in said housing for collecting energy from a surrounding environment to recharge said power system, said energy collection system including a solar cell array or a thermo-electric device having a thermal mass in thermal communication with a surrounding medium for generating a voltage potential in response to a thermal potential difference across said thermal mass and the surrounding medium; and a system controller including a programmable digital processing device mounted in said housing for controlling operations of said sensor suite, said data storage resource, said dive control system, said data communications system, said locating system, said rechargeable power system and said energy collection system.

22. An automated method for obtaining environmental data in an ocean or fresh water body comprising the steps of:

deploying into an ocean or fresh water body a portable free drifting instrument package including sensor means for collecting environmental data samples, storage means for storing environmental data samples, dive control means for positioning the instrument package over a range of depths, data communication means for providing data communications with one or more remote receiving stations, location means for determining a position of the instrument package, rechargeable power means for providing operational power to the instrument package, energy collection means for recharging said power source, and system control means for controlling operation of said sensor means, said storage means, said dive control means, said data communications means, said locating means, said rechargeable power means, and said energy collection means;

controlling said instrument package to obtain and store environmental data samples over a selected range of depths while freely drifting in the ocean or fresh water body;

controlling said instrument package to periodically surface;

controlling said instrument package, upon surfacing, to obtain a position;

controlling said instrument package to transmit said position and said stored environmental data samples to a remote receiving station;

controlling said energy collection system to periodically recharge said rechargeable power supply, as necessary; and controlling said instrument package to reside below the photic zone for a period of time sufficient to substantially eliminate biofouling.

23. A portable free drifting instrument package for cyclically collecting oceanic and/or fresh water environmental data over a range of depths, comprising:

a submersible housing;

a sensor suite mounted to said housing for collecting selected environmental data relating to a surrounding medium;

a data storage resource mounted to said housing for storing environmental data sensed by said sensor suite;

a dive control system mounted to said housing for controllably positioning the instrument package at a selected depth;

a data communications system mounted to said housing for facilitating bi-directional (full duplex) communication between the instrument package and a remote communications site;

a locating system mounted to said housing for self determination of navigational position of the instrument package;

a rechargeable power system mounted to said housing for providing operational power to the instrument package;

an energy collection system mounted to said housing for collecting energy from the environment to recharge said power system, said energy collection system including a horizontal and/or vertical solar collector and thermo-electric device; and a system controller mounted to said housing for controlling operations of said sensor suite, said data storage resource, said dive control system, said data communications system, said locating system, said rechargeable power system and said energy collection system.

24. The instrument package of claim 23 wherein said solar collector includes a plurality of photo voltaic cells.

25. The instrument package of claim 23 wherein said thermoelectric device includes a Peltier device with no moving parts.

26. The instrument package of claim 25 wherein said Peltier device includes a thermal mass in thermal communication with a surrounding medium, said thermal mass being selected to provide a voltage differential across said Peltier device proportional to a thermal differential across said thermal mass and the surrounding medium.

* * * * *